March 10, 1959 H. KLEINE Plant Pat. 1,816
PYRACANTHA ANGUSTIFOLIA PLANT
Filed June 23, 1958
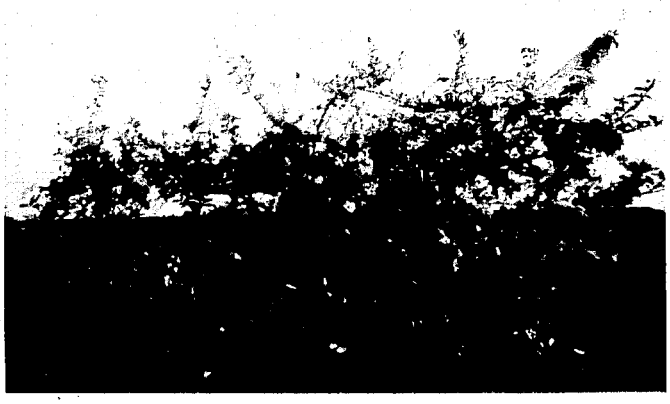
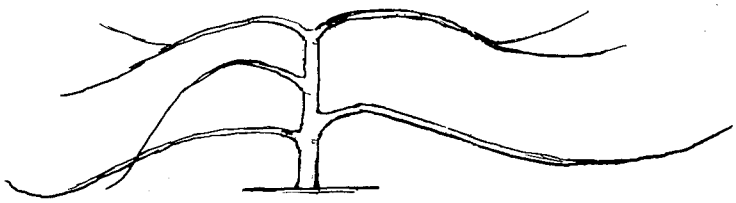
INVENTOR
Henry Kleine
By Orville M Kile
Plant Pat. Agt.

United States Patent Office

Plant Pat. 1,816
Patented Mar. 10, 1959

1,816

PYRACANTHA ANGUSTIFOLIA PLANT

Henry Kleine, Newport, Mich.

Application June 23, 1958, Serial No. 744,028

1 Claim. (Cl. 47—59)

My present invention consists of an improved variety of Pyracantha plant of the *angustifolia* type, the improvement being inherent in the type of growth.

A typical plant of *Pyracantha angustifolia* type will grow to six feet in height, while a plant of my new variety of the same age will grow about 15 inches high but with its branches extending almost horizontally, from a central stem. While it is true that sometimes the typical *Pyracantha angustifolia* will have prostrate branches, the main growing habit is upright and the prostrate branches merely droop instead of being extended horizontally.

My new variety is the result of selection of numerous seedlings of *Pyracantha angustifolia* grown by me at my nurseries in Newport. The exact parentage is not known.

I have asexually reproduced the new variety of my nurseries in Newport, Michigan, by means of layering, and the novel growth characteristics appear to be permanent.

The accompanying illustration shows a color photograph of a plant of my new variety, in approximately its true colors; also a black-and-white diagrammatic sketch indicating the horizontal growth of the branches as opposed to the usual upright growth of the typical *Pyracantha angustifolia.*

No claim to color is made, and the color designations in the following description indicate the usual dictionary meaning of the terms.

*The plant, flower, and fruit*

Growth: Low-growing shrub, with spreading branches extending almost horizontally from a central stem. A typical plant grows to approximately 15 inches in height.

Foliage: Leaves alternate; short-petioled; half-evergreen. Leaves—obtuse; usually recurved at margin; dark green above and grayish green on under surface; narrow, typical leaf measuring approximately 1¼ inches by ½ inch.

Stems: Long; slender; strong.

Flowers:

*Borne.*—In short-stalked corymbs of few flowers.
*Petals.*—Rounded and spreading.
*Color.*—White, with prominent yellow-anthered stamens.

Fruits:

*Quantity.*—Numerous.
*Arrangement.*—Small clusters.
*Color.*—Bright orange.
*Size.*—¼ to ⅓ inch in diameter.
*Shape.*—Depressed-globose.

Having thus disclosed my invention, I claim:

The new and distinct variety of *Pyracantha angustifolia* plant, substantially as herein shown and described, characterized particularly as to novelty by its low growth in which its branches extend from a central stem in an approximately horizontal position.

No references cited.